United States Patent [19]

Kirschenbaum et al.

[11] Patent Number: 5,217,379
[45] Date of Patent: Jun. 8, 1993

[54] PERSONAL THERAPEUTIC DEVICE AND METHOD

[75] Inventors: Daniel S. Kirschenbaum, Evanston, Ill.; Harold J. Kramer, Springwater; Mark W. Smith, Scottsville, both of N.Y.

[73] Assignee: Digital Therapeutics, Inc., Evanston, Ill.

[21] Appl. No.: 745,068

[22] Filed: Aug. 14, 1991

[51] Int. Cl.⁵ ............................................. G09B 19/00
[52] U.S. Cl. ...................................... 434/236; 131/270
[58] Field of Search ............... 434/236, 237, 238, 308, 434/319, 320, 321; 131/270; 364/419, 569; 369/19

[56] References Cited

U.S. PATENT DOCUMENTS

| | | | |
|---|---|---|---|
| 2,305,283 | 12/1942 | Theilkas | 434/238 X |
| 3,647,991 | 3/1972 | Gaon et al. | 179/100.25 |
| 3,655,325 | 4/1972 | Toppel | 434/236 X |
| 3,691,652 | 9/1972 | Chynes | 434/236 |
| 3,782,006 | 1/1974 | Symmes | 434/236 |
| 3,825,947 | 7/1974 | Rubin et al. | 369/19 X |
| 3,986,136 | 10/1976 | Hurlburt | 331/78 |
| 4,035,930 | 7/1977 | Lambert | 434/319 X |
| 4,384,855 | 5/1983 | Walsh | 434/238 |
| 4,615,681 | 10/1986 | Schwarz | 434/236 |
| 4,682,299 | 7/1987 | McIntosh et al. | 340/309.4 X |
| 4,710,145 | 12/1987 | Hall Vandis | 446/100 |
| 4,812,126 | 3/1989 | Gilliksen | 434/238 |
| 4,853,854 | 8/1989 | Behar et al. | 131/270 |
| 4,900,256 | 2/1990 | Dara-Abrams | 434/236 |

OTHER PUBLICATIONS

"Motivaider" (Brochure); Behavioral Dynamics, P.O. Box 66, Thief River Falls, Minn. 56701, Jun. 6, 1988.
Dictaphone Model 4250 operation manual and schematic drawing, undated.

Primary Examiner—Jessica J. Harrison
Attorney, Agent, or Firm—Cumpston & Shaw

[57] ABSTRACT

A programmable microprocessor-controlled cassette recorder/player plays messages in accordance with the programming of the microprocessor, to a client. The client either actuates the recorder/player on his or her own, or when prompted to do so by the microprocessor. The messages have a behavior-modifying thrust, and may be in the voice of the client's therapist.

10 Claims, 7 Drawing Sheets

PERSONAL THERAPEUTIC DEVICE AND METHOD

FIELD OF THE INVENTION

The present invention relates to personal therapeutic devices, particularly for use in modifying behavior.

The Prior Art

| U.S. Pat. Nos.: | |
| --- | --- |
| Gaon et al | 3,647,991 |
| Hurlburt | 3,986,136 |
| Schwartz | 4,615,681 |
| Hall Vandis | 4,710,145 |
| Dara-Abrams | 4,900,256 |

In addition, about June 24, 1988, Behavioral Dynamics, P.O. Box 66, Thief River Falls, Minn. 56701, published a four page brochure with the title "MotivAider".

Gaon et al discloses a "programmed time-responsive audio message and reminder device. Among other things, it is said that it could be used to present a "self-improvement" message to persons engaged in their normal daily activities. No other details as to the nature or purpose of the messages are disclosed.

Hurlburt discloses randomly periodically analyzing a subject's behavior for modifying it by rewarding or punishing the subject, as may be appropriate.

Hall Vandis discloses a doll which in essence simulates a human being. The doll is given to a child who activates the doll so that it plays back to the child a message such as the person simulated, a family member, for example, might have for the child, by way of cheering the child. No other details as to the nature of the message or of the simulated being are disclosed. The child may use the doll to communicate with family or a therapist. No behavior modification is provided for, and the emphasis is on comforting, and on enhancing relationships.

Schwartz is a cigarette dispenser for monitoring and analyzing an individual's smoking habits. By timing cigarette dispensing and emitting messages and other stimuli, the dispenser attempts to discourage the user from smoking cigarettes from the dispenser.

Dara-Abrams device is a therapeutic toy for helping children to learn how to express emotion adaptively, whereby to decrease the incidence of temper tantrums, aggressive acts, or other problematic emotional reactions that have immediate impact on the environment. The toy plays back a standardized message by a therapist.

MotivAider is a device which periodically emits an alerting signal which, when perceived by the user of the device, is supposed to make the user think of some personal objective he should have in mind, but might not think of enough to pursue effectively, unless reminded.

SUMMARY OF THE PRESENT INVENTION

In the present invention, a personal therapeutic device plays back to its user a recorded message having a semantic content relating to modifying certain behaviors of the user. The playback may occur at intervals, random or regular, either in response to programming of the device, or to remote actuation by the user's therapist, counselor, or any other individual involved in the user's behavior modification process. (Hereinafter therapist is to be taken to mean either therapist, counselor, or any other individual involved in a helping relationship to a second individual, or to a group.)

The user can also, or instead, activate the device to playback the message to him or her, or them, and there may be several messages to be chosen from or played back in sequence, each of which has semantic content relating to modifying the behaviors in question.

The device may also provide for the user recording a message for playback to the therapist. When the original message or messages have been recorded on a medium, such as cassette tape, the tape will have space following prerecorded messages, whereby to provide for recording the user's messages in association with related prerecorded messages.

The general object of the present invention is generally to assist a user thereof in modifying his or her behaviors, and in particular, in maintaining attentional focus on the modification process, vigilance with respect to target behaviors, and the process of modification, and as well, help the user keep in mind difficult goals of the modification process.

Another object of the invention is to assist in modifying the user's behavior by means of messages whose semantic content is derived from user-therapist interaction in the course of directing said user's attention to behaviors targeted for modification, and of helping the user to refocus his or her attention on certain thoughts and cognitions in order to modify said behaviors in accordance therewith over time.

Other objects of the invention include providing a personal therapeutic device and method which improves client motivation, enhances, and makes more effective the client-therapist relationship, doing so substantially independently of the theoretical, technological or scientific orientation of the therapist.

In particular, according to the present invention, an improved recorder/player has control means providing for easy and economical use of said recorder/player as a personal therapeutic device.

Still other objects of the invention will be evident from the following description of the present invention.

Virtually all major psychotherapeutic approaches attempt to get clients to talk to themselves in a new, different, and presumably healthier way. Psychoanalytically oriented interventions focus on strengthening ego structure, quite frequently including the enhancement of individuation. This involves fostering a new sense of self in which the patient develops and accepts an identity different from his or her family. The patient makes this dramatic change by "introjecting" a new self, or talking to him or herself, using the interactions that occur in therapy as a framework.

Cognitive-behavior therapies embrace a similar process of change, albeit a process that ostensibly seems very different from analytical approaches. Clients are taught in cognitive-behavior therapies how to modify their "self-statements", "self-instruction", or "irrational thinking". This approach focuses less on the global construct of "the self" and more directly on how self-statements impact on specific types of maladaptive or non-adaptive responses, such as undesirable behavior, anxiety, pain, depression, and performance of cognitive and motor tasks.

The process of teaching people how to talk to themselves more effectively is a nearly universal mission of seemingly diverse clinical interventions. It is also one of the only known elements or parts of the clinical enterprise that has been shown to produce very significant and positive results.

The present invention, a personal therapeutic device, or PTD, provides a means for therapists of all theoretical persuasions to continue the process of teaching clients how to talk to themselves—beyond the confines of the therapist's office. The PTD is programmable with as many as sixty 10-second sets of statements, either with the client present or as an independent supplement to face-to-face intervention, when the client is absent. These sets of statements are heard by the client throughout the course of his or her day, every day, all week. All the client does is take a small light PTD out of a pocket or purse when it beeps, say every 30 or 40 minutes in the client's waking day, press a button, and hold it to an ear to hear one of the sets of statements. For example, for someone in a weight control program, the messages could remind the weight controller to keep track of ("self-monitor") food intake and exercise expenditure. Messages could also prompt planning for "high risk situations" provide coping statements and ideas, reassure the client, and remind him or her of the reasons for attempting to make lifestyle changes.

Preferably, the particular message the client hears will be selected randomly in order to help maintain and enhance interest in, and involvement with, the messages. The net result exponentially expands the instructional, therapeutic and/or behavior modifying impact of the therapeutic process.

The PTD will be is especially helpful in promoting long-term maintenance of the client's behavior change. People usually fail to maintain behavior changes, particularly those that are self-regulated, and that involve powerful physiological opponent processes. This failure in the maintenance of therapeutic change, sometimes described as self-regulatory failure, includes a number of active elements.

BRIEF DESCRIPTION OF THE DRAWINGS

FIGS. 8-1, 8-2, 8-3, and 8-4 form a detailed diagram of the circuitry of the PTD, as present constituted.

DETAILED DESCRIPTION OF THE INVENTION

Figure 1:
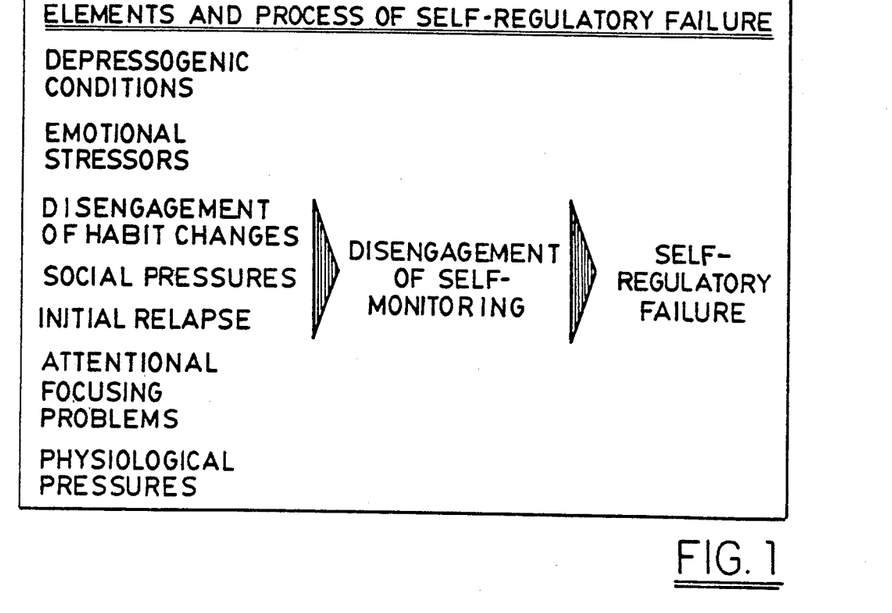
FIG. 1 is an outline of the elements of the concept of self-regulatory failure.

Of the eight elements in self-regulatory failure shown in FIG. 1, "disengagement of self-monitoring" is considered most fundamental (Kirschenbaum, 1987). The evidence indicates quite clearly that "self-monitoring", or systematically attending to, and keeping track of, target behaviors, is necessary for effective self-regulation. When people discontinue self-monitoring, they often fail to maintain changes in behavior. As FIG. 1 shows, many stressors can lead to discontinuation of self-monitoring. On the other hand, some recent research shows that maintaining therapeutic contact can prevent discontinuation of self-monitoring.

Use of the PTD will make it more difficult to discontinue self-monitoring, and also will help patients sustain their awareness of the behavior change regimen, their goals and the techniques that can help them succeed. Likewise, extended contact with the PTD can help prevent self-regulatory failure, as for example, by providing the user, who is attempting self-regulation, with statements of self-reward strategies, positive self-statements, and messages that prevent or counteract use of negative or punitive self-statements. For example, people often maintain necessary weight-reduction habits (Stalonas & Kirschenbaum, 1985) as long as they are in close contact with a supportive, well-conducted therapeutic group or individual. Very brief weekly contact with therapists by phone and mail, when added onto a behavioral treatment program, substantially improves the notoriously refractory problem of maintenance of weight losses long term. Even better, extending initial group sessions and using sustained weekly contact, produce and maintain long term, large average weight losses. These effects were obtained using methods safer than others capable of producing similar losses such as protein-modified fasting.

The present invention will help prevent self-regulatory failure, without requiring the user to maintain sustained direct contact with the therapist. It will do this while serving as a means to sustain self-monitoring that is relatively unobtrusive and high enough in intrinsic interest to be maintained by the user. The PTD can be programmed by the user, after working with it under the therapist's supervision and after achieving therapeutic goals. The client would only have to continue using the PTD to be reminded of his or her progress, reasons for changing, how to attend to target behaviors, and other useful messages. The use of many different messages, access to changing them as desired, random access to same, and great flexibility in types of statements will maximize its effectiveness in this regard. Also, periodic sessions with the therapist or a paraprofessional (specially trained for this task) will enhance its appeal and lead to sustained use. In addition, for more severely disturbed individuals (e.g., borderline personality disorders), the kind of sustained contact which they need for maintenance of treatment efficacy, will be provided by the present invention.

Finally, in the past the efficacy of self-help groups, even with some therapist assistance, has not been encouraging. This is especially true with regard to refractory problems such as weight reduction. The present invention will augment self-help effects toward more clinically useful results than heretofore.

A personal therapeutic device (PTD) of the present invention is essentially an intelligent prgrammable mini-tape recorder/player. Therapists can easily program these devices, say be personal computer, to record a large number of messages to remind patients of important goals or motivators, encourage them to use constructive self-statements, and promote retention of key therapeutic insights. The PTD functions like a pager than can signal (or "beep") the patient at regular intervals throughout the day (e.g., every 40 or 60 minutes). Upon hearing the signal, the patient presses a playback button and listens to one of the messages. This function greatly enhances the frequency of attention to key issues of target behaviors in the patient's everyday life. The patient can also listen to a message at any time by simply pressing a playback button. In addition, the PTD may have the capability of recording a patient's responses to the messages, from patients, a feature which is especially useful for the assessment of conscious feeling states and physiological processes involved in the modification of health and illness-risking habits. A special low-cost programming unit can replace programming with a personal computer, which will enable the many therapists who do not use PCs to program the PTD quite easily.

In addition to the more or less conventional playback/record tape unit, the PTD has a micro-controller with internal ROM and RAM, built-in timers, and a 3-wire asynchronous serial port. In addition, the software to drive the micro-controller is stored in the internal ROM providing more than enough storage for the envisioned tasks and low power consumption for extended battery life.

Figure 2:
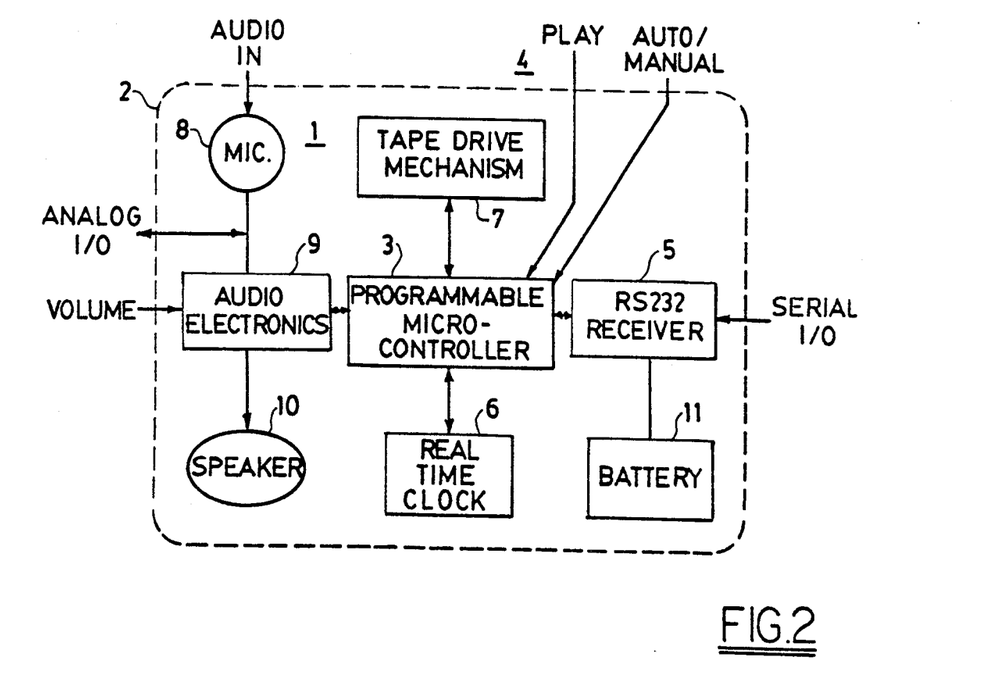
FIG. 2 is a schematic diagram of a personal therapeutic device (PTD) according to the invention.

In accordance with the invention, the elements of a personal therapeutic device, designated generally by the reference numeral 1, are contained within a suitable housing 2 depicted in broken line as it can take many forms.

The heart of the PTD 1 is a programmable micro-controller 3, controlled in part by an auto/manual switch 4, the function of which will be explained later. An RS232 transceiver 5 and a real-time clock 6, the former providing a serial input/output port, and the latter providing for timing the operation of the PTD 1, as will be later explained in more detail.

The items 3 through 6 are unique to the PTD 1, and distinguish it from a conventional cassette recorder/player unit according to the prior art. However, like a conventional unit, PTD 1 has the usual playback means consisting essentially of tape drive mechanism 7, internal microphone 8, audio electronics 9, speaker 10, battery 11 and play switch 12 (note, however, that unlike in the conventional unit, the play switch 12 acts through programmable micro-controller 3.) Not shown, but which may also be present, is a conventional unit's set of stop, pause, rewind, fast forward, play back and record switches, which is capable of conventional control of the items 7 through 10, independently of items 3 through 6, and 12. Also not shown are the provisions in the tape drive mechanism for receiving a conventional tape cassette for recording/playing a therapeutic program according to the present invention. Insofar as are concerned the conventional elements of the PTD 1, such cassette cooperates therewith in the usual fashion, until or unless the therapeutic aspect of the PTD is put into operation.

Figure 3:
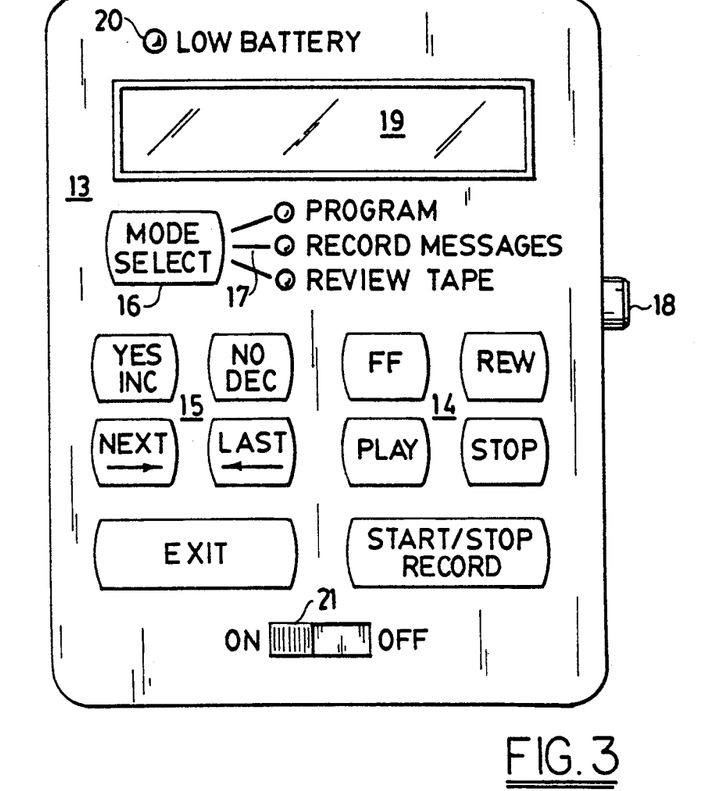
FIG. 3 illustrates a programming unit for said PTD.

FIG. 3 shows a control layout for a programming unit 13. Thus, reference numeral 14 denotes a group of five switches labeled in accordance with function: FF, fast forward; REW, rewind; PLAY, STOP and START/STOP RECORD (repeated actuation of which alternately starts and stops recording.) The functions controlled by group 13 are those of a conventional play/record cassette mechanism (not shown) in unit 13.

According to the invention, another group 15 of switches labeled YES/INC, NO DEC, NEXT, LAST and EXIT, provide for answering messages during the programming mode.

A switch 16, MODE SELECT, provides for selecting PROGRAM mode, in which a PTD connected to the serial port 18 can be programmed therethrough; RECORD MESSAGES provides for storing messages onto tape; and REVIEW TAPES provides for scanning messages already stored on tape. Switch 16 may be of the type wherein successive actuations cycle the programming unit through the modes indicated by label on the FIG., while the appropriate one of a group 17 of three indicator light indicates which mode is on at any given instant. The serial port 18 provides for connecting a cable (not shown) to the transceiver 5 of the PTD of FIG. 2. A 2×16 liquid crystal display 19 provides for questions and information. Other conventional features may be supplied, such as the LOW BATTERY indicator 20, and an on-off switch 21 for connecting and disconnecting the unit from its power supply: battery or AC/DC converter.

Figure 4:
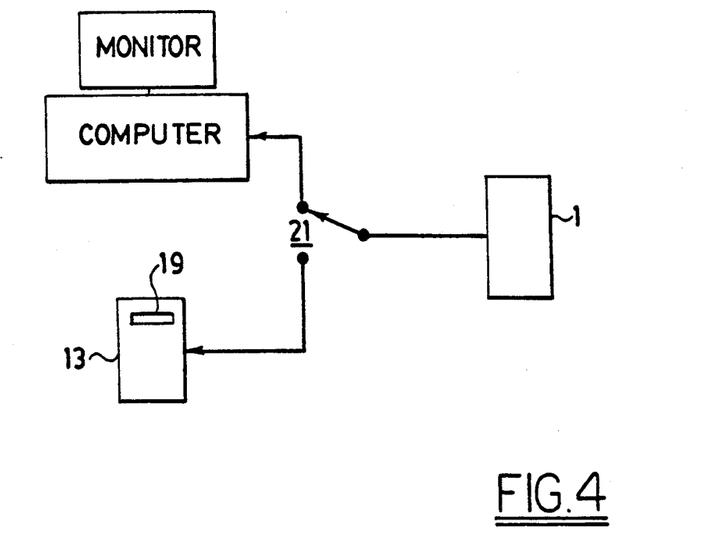
FIGS. 4 and 5 respectively show a playback only system for said PTD, and the tape format used therein.

In FIG. 4, a PTD 1 is shown as alternately connectable, as by a switch 21, to either the serial port of the programming unit 13, or to a serial port (not shown) of a conventional personal computer with monitor, i.e., a so-called PC, which has an RS232 transceiver (not shown) like the PTD 1 and programming unit 13. In practice, only one of these alternatives need to be used, depending on considerations such as portability, cost and so on.

FIG. 4 shows PTD 1 connected to the PC, but not to unit 13. (Applicants have used a Commodore "VIC20" as the PC, but at this time an IBM-compatible computer is preferable).

When the PC begins the program, the following screens, which describe the program and prompt the computer operator, appear.

Screen 1

MESSAGE RECORDING PROGRAM

The procedure that follows will enable you to setup the PTD to play a series of messages recorded on tape. After selecting from a list of playback options, you will be asked to record messages onto tape. Before proceeding, make sure the following steps have been taken:
1. Using the cable provided, connect the DIGITAL THERAPIST to the serial (RS232) port on the computer.
2. Install a microcassette tape in the DIGITAL THERAPIST.
 PRESS ANY KEY TO CONTINUE Screen 2

The PTD has a button (PLAY) and a switch (MANUAL/AUTOMATIC) on the front panel that are controlled by the user:
1. PLAY button: Whenever this button is pressed, a message is played immediately.
2. MANUAL/AUTOMATIC switch: In the MANUAL position, the PTD will not signal the user to PLAY a message. The user decides when to press the PLAY button.
 (This position should be selected at nighttime or whenever the user does not wish to be disturbed.)
 In the AUTOMATIC position, the unit will signal the user at predetermined time intervals to PLAY a message. The PLAY button must then be pressed to turn off the signal and play the message.

You are now ready to select playback options for the PTD.
 PRESS ANY KEY TO CONTINUE Screen 3

The PTD will always play a message when the PLAY button is pressed, independent of the MANUAL/AUTOMATIC switch position. In the AUTOMATIC position the unit will also signal the user at predetermined intervals to PLAY a message (for example, every hour or every two hours) if you select the automatic playback option. Do you want to select the automatic playback option?
Press Y or N

Screen 4

You have selected the automatic playback option. Specify the desired time interval between messages.
Enter NUMBER OF MINUTES followed by RETURN

Screen 5

You have the option of keeping the time interval fixed at 40 minutes or randomly varying the interval by as much as 10 minutes. Do you want the time intervals to vary randomly?
Press Y or N
N.B. The intervals specified here are merely by way of example.

Screen 6

You have completed the selection of playback options:
The PTD has been programmed to signal the user at 40 minute intervals (randomly varied by as much as 10 minutes) when the MANUAL/AUTOMATIC switch is in the AUTOMATIC position. Messages will be played back sequentially (as recorded on tape). Please select one of the following three options:
1. If you would like to change any of the selections listed above, press C.
2. If you are ready to begin recording new messages onto tape, press R.
3. If you have already recorded messages onto tape and wish to exit this program, press E.
N.B. The result of pressing C or E is obvious, whereas pressing R will cause the program to continue with screens 7 through 12, as follows:

Screen 7

MESSAGE RECORDING

The DIGITAL THERAPIST is now ready to store your messages onto tape. You can record as many unique messages as you would like, limited only by the 30 minute capacity of the tape. After each message is recorded, you will have 3 options:
1. Record another message
2. Change the previous message
3. End the recording session
To begin recording the first message, press SPACE and get ready to speak into the microphone. If you do not wish to record any messages, press E.

Screen 8

MESSAGE RECORDING

RECORDING

SPEAK INTO MICROPHONE

Press SPACE when you are finished with your message.
N.B. The last "RECORDING" blinks.

Screen 9

MESSAGE RECORDING

You have just recorded message number 1:

1. To begin recording message number 2, press SPACE and get ready to speak into the microphone.
2. To change the previous message, press C and wait for instructions.
3. If you are finished recording, press E.

Screen 10

MESSAGE RECORDING

REWINDING TAPE OVER PREVIOUS MESSAGE PLEASE WAIT

N.B. This screen blinks, and is automatically followed by screen 11.

Screen 11

MESSAGE RECORDING

There are currently 9 messages stored on tape!
Are you sure you are finished recording messages?
Press Y or N

Screen 12

The DIGITAL THERAPIST is ready for use!
Disconnect the DIGITAL THERAPIST from the computer.

This extremely user-friendly program enables a therapist to record messages, change them, and set the various parameters involved with using the PTD. The therapist simply follows the programs as above, using a floppy disk and conventional personal computer, such as IBM "PC" compatible machine. The program instructs the user (the client or therapist) about each aspect of the PTD and how to use it. It first reminds the user to plug in a cable between the PC and the PTD, using the serial port on the PC and the serial port connector socket on the PTD. Next, it describes the Play button and the Manual/Automatic switch. (When the play button is pressed, a message will play immediately. When the Manual/Automatic switch is in the Manual position, the PTD will not signal the user (client) to play a message; only when the switch is in the Automatic position will it "beep" the user (client) at the interval set by the therapist. The beep or signal is intended as a prompt. When the user hears it, he or she will need to play a message in order to turn off the beeping sound.) The program then instructs the user about the various options, such as the automatic playback option. The user (therapist) must then decide: whether to use the automatic playback option, the time interval to be used between beeps (in the automatic playback condition only, of course), and whether or not to have the time interval remain constant or to vary randomly by a few minutes. As shown, the final page of the program summarizes the choices of options made by the therapist and then offers the opportunity to change or or them or to go on to start recording messages or to exit the program. The recording process is similarly simple and user-friendly. All recording and changing of messages occurs via the computer. The therapist merely hits the space bar when he or she wises to begin recording and hits it again to signal the end of a message. The PTD puts the appropriate amount of space between messages and the recording program advises the therapist of the number of messages recorded as they accumulate. After finishing the recording process, the program allows the user (therapist or client) to terminate the session by hitting one key ("E"). The PTD then puts down some blank space on the tape to signal the end of the recorded messages. Once the patient reaches the final message, the PTD automatically rewinds to the beginning.

In a preliminary clinical trial of the present invention, the recorded messages were generated at weekly meetings between therapist and patients. The number of messages per individual ranged from 18-31, and were brief phrases or sentences designed to encourage the patients and prompt them toward certain habit changes. For example, all patients in one group wanted messages reminding them that they were "building on a foundation of success" and messages that encouraged them to self-monitor (to record food eaten in writing). Other examples were: "Remember to plan for that party Saturday night. What will you eat beforehand? What will you do while there to keep in control? " "Fruit is fine; just watch the quantities." "You can feel complete without something sweet!" "You feel so good when you are in control." "Why let food control you, when you can control it? ""Some soothing alternatives to high calorie eating include brief walks, baths or showers, low calorie treats." "Losing weight will keep you in more stylish clothes and feeling better physically." "Is eating worth the self-hate? ." "Be kind to yourself; remember the powerful biological forces that you are battling."

The patients in question were several obese individuals who, despite participation in a high quality weight control program had been unable to lose weight in a period of one month or more immediately preceding intervention with the PTD. A few weeks of daily use of the PTD saw each subject begin to lose weight and exhibit management in mood and in control of situational overeating. It appears at this time that the active ingredients in the intervention were self-statement modifications, and increasing self-focused attention and self-monitoring.

The foregoing description of the software program is realizable in a variety of hardware systems. In the present case, FIGS. 8-1, 8-2, 8-3, and 8-4, show the best mode of PTD construction which we know of so far for the practice of our invention, both in terms of the software and of the diagrammatic illustration of FIGS. 2 through 7.

We turn now to these FIGS. to elucidate the foregoing in terms of specific hardware, especially the electrical circuitry. The major portion of the overall circuit is that of a conventional tape recorder/player which applicants adapted to the purposes and functions of their PTD. The minor portion thereof, essentially switch S2, chips U1, U10, U9A, and U8, and the circuitry which interconnects them, represents what applicants have added for so adapting the conventional machine. While as shown the recorder/player electronics share the same platform with the PTD electronics, the former and the latter could have their own circuit boards. Preferably both share the same board (not shown).

Figure 82:
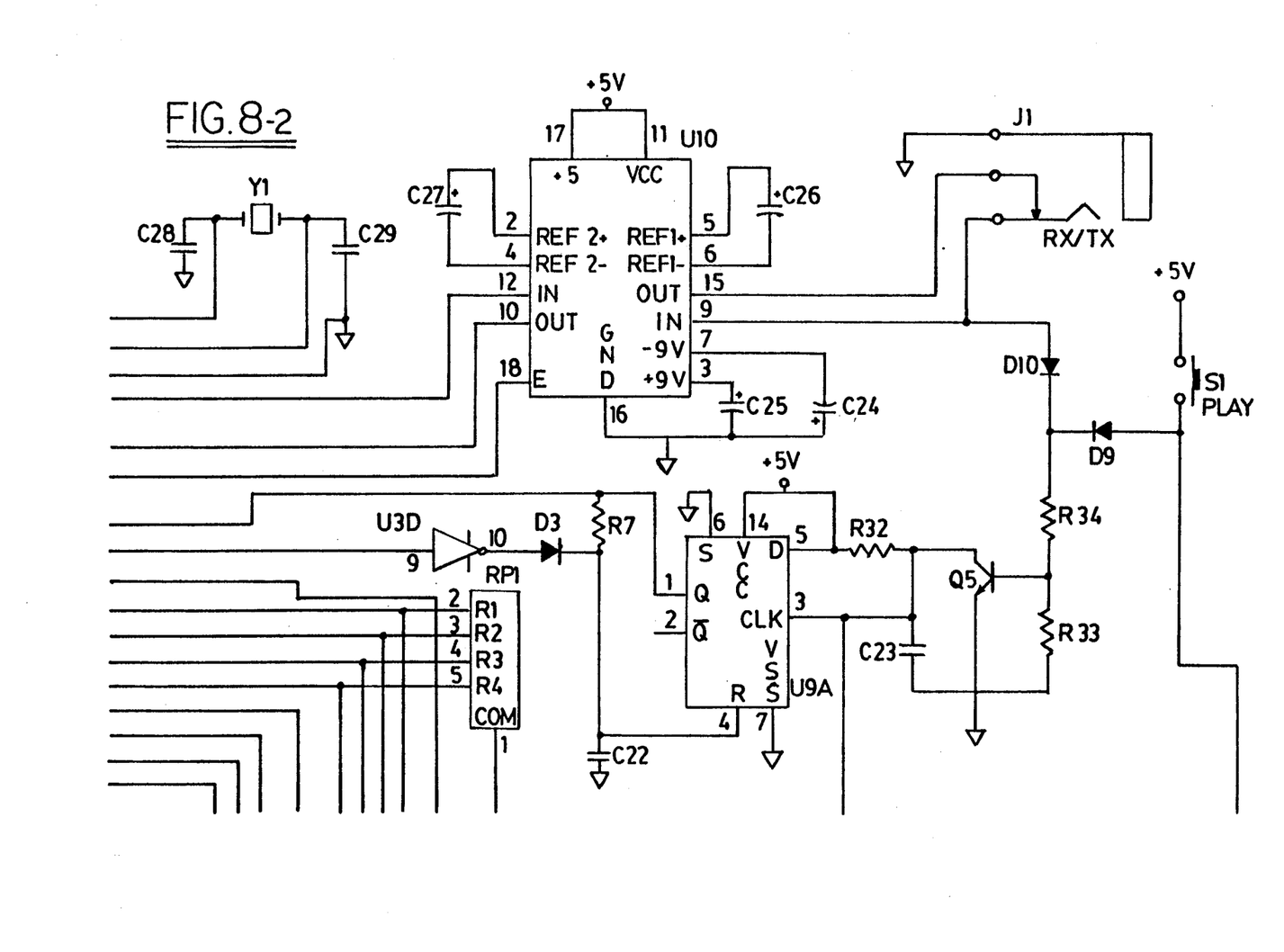
Figure 83:
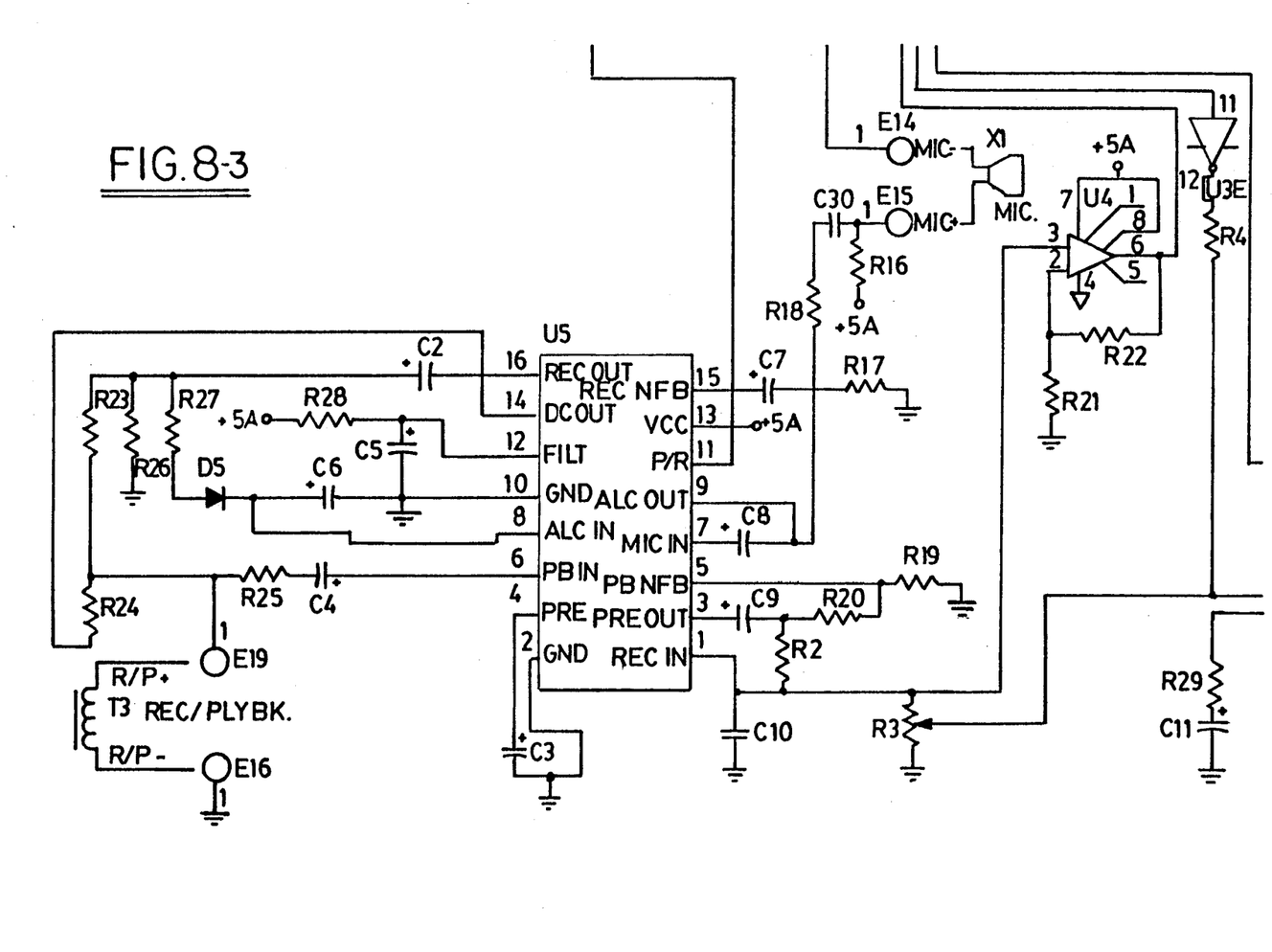
Figure 84:
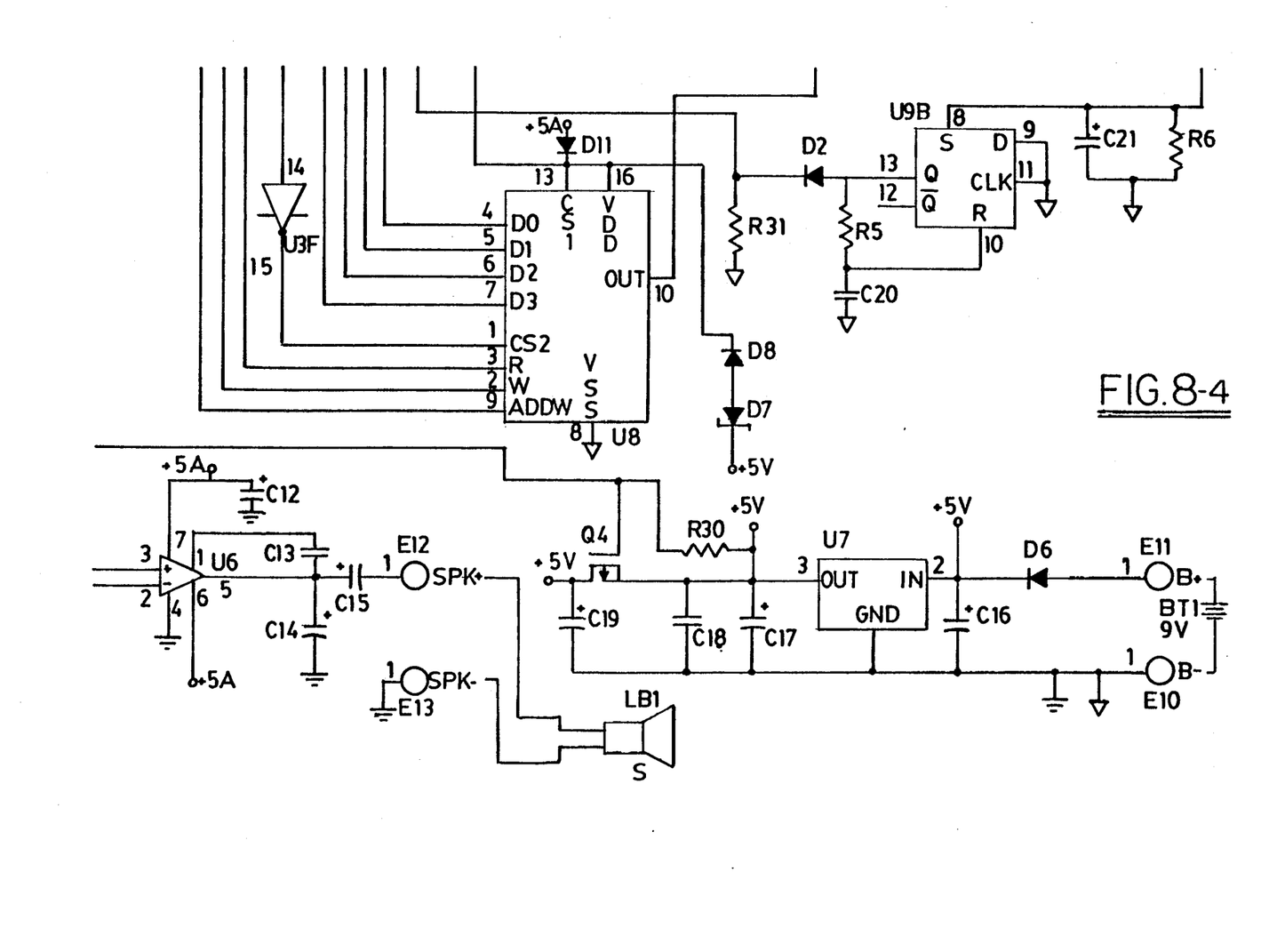

In FIG. 8-2, S1 is the play switch corresponding to switch 12, FIG. 2, and S2 corresponds to auto/manual switch 4, of that FIG. The chip U10 provides the RS232 transceiver 5, and there is a jack J1 to provide for serial input/output. Programmable micro-controller 3 is provided by chip U1, which is a microprocessor, and real-time clock 6 is provided by a clock chip U8.

Insofar as programmable micro-controller 3 is concerned, actuating S1 wakes it up, so to speak. In normal use, except for the real time clock 6, the PTD is energized only when the controller 3 determines that its programming is commanding that the PTD do something. Actually, the clock 6 energizes the controller 3 once per second to enable the controller to check on what its programming calls for, if anything. A small amount of power is used by the controller to keep alive the program stored therein, but as long as the patient is merely going about his or her daily rounds, the PTD uses substantially no power from battery BT1. As a result, battery life can be an order of magnitude or more greater than if controller 3 is continuously energized.

The voltage from battery BT1 is regulated by a regulator U7, which furnishes voltage to both the clock U8 and the recorder/player portion of the PTD. When the clock wakes up the microprocessor, and the latter finds that the PTD has something to do, so to speak, it turns on the FET switch Q4. Q4, when off, prevents the recorder/player elements from using power, but when on allows the current to flow thereto, if and when power using activity is called for by the program.

When the switch S2 is in MANUAL position, the patient can push the switch S-1, which will tell the controller 3, when it wakes, that the patient wishes to hear a message, and, so instructed, the controller will actuate the recorder/player to play a message.

With S-2 in the AUTO position, when the controller 3 wakes up and finds that enough time has elapsed, it actuates the beeper. The beeper will sound until the patient actuates S1, the play switch. Actuating the play switch turns the beeper off, and causes the controller to run its program.

In other words, actuating S1 wakes up the controller 3 so that it plays a message on the tape, regardless of the position of the auto-manual switch S2, i.e., the switch S2, when S1 is actuated, may be in either auto or manual position. If S2 is in the manual position, the user is requesting that a message be played without being prompted to do so by the PTD, but if S2 is in the auto position, the user must push S1 in response to beeping to discontinue the beeping. As soon as S1 is pressed, the beeping is discontinued and a message is played.

The controller 3 wakes up, of course, in response to programming by the PC or the programming unit 13. The programming instrumentality produces a serial digital output which reaches the controller 3 via the serial port, i.e., jack J1 in FIG. 8.

The programming unit 13 is in essence a dedicated computer, which the PC of FIG. 4 emulates. Essentially, there will be no functional difference, but the LCD screen of the PTD obviously will not be able to display the full text of the screens, as set forth supra. However, since the prompts to the operator, and other essential displays can be handled by the LCD screen, then a manual explaining the LCD displays will be provided for the operator's benefit in using the programming unit.

Figure 5:
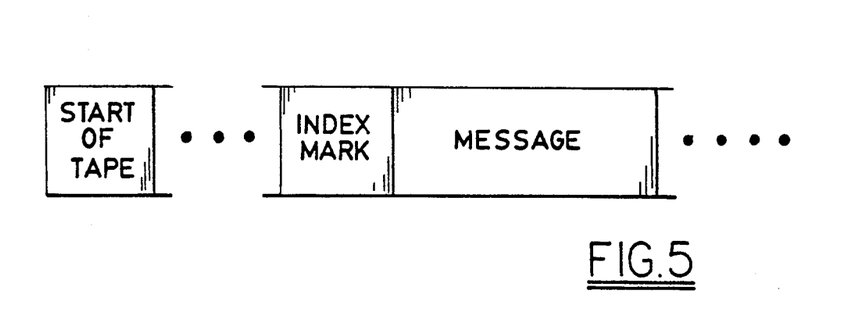

The invention as shown in FIGS. 4 and 5 can be readily modified to allow the patient to respond to the PTD's messages. Such modification is essentially but a matter of providing some blank tape immediately following any message or messages to which patient-response is desired. Preferably, between any such message, like in a telephone answering machine, there will be a patient prompt between that message (at the end thereof, in reality) and the response space.

The patient may also be directed to push a button or the like, to get the programmable micro-controller to put the PTD into a record mode.

The response feature may be provided for in the above-described MESSAGE RECORDING PRO- GRAM. Since the PTD is intended to create, in some degree, the effect of the therapeutic dialogue or interchange, the effect will obviously be enhanced if the patient is able to respond immediately to questions, suggestions, etc., of the therapist, right after they are made.

Figure 6:
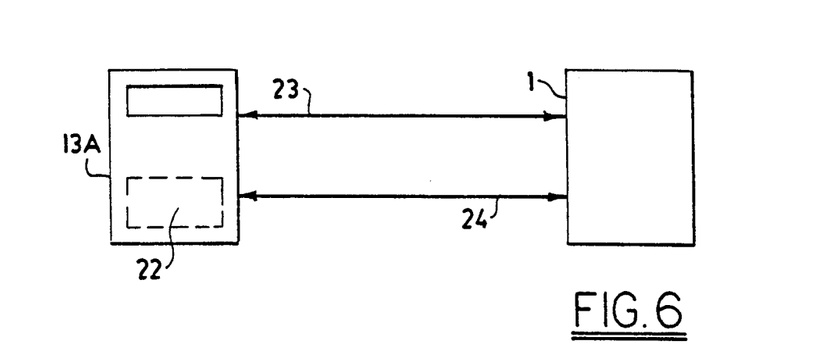
FIGS. 6 and 7 respectively show a user-response recording system for said PTD and the tape format used therein.
Figure 7:
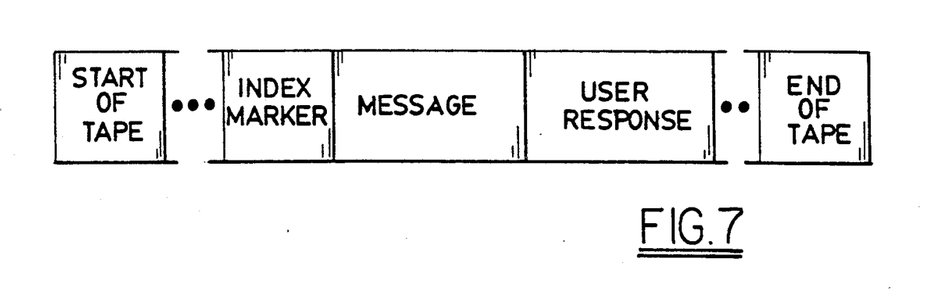
Figure 81:
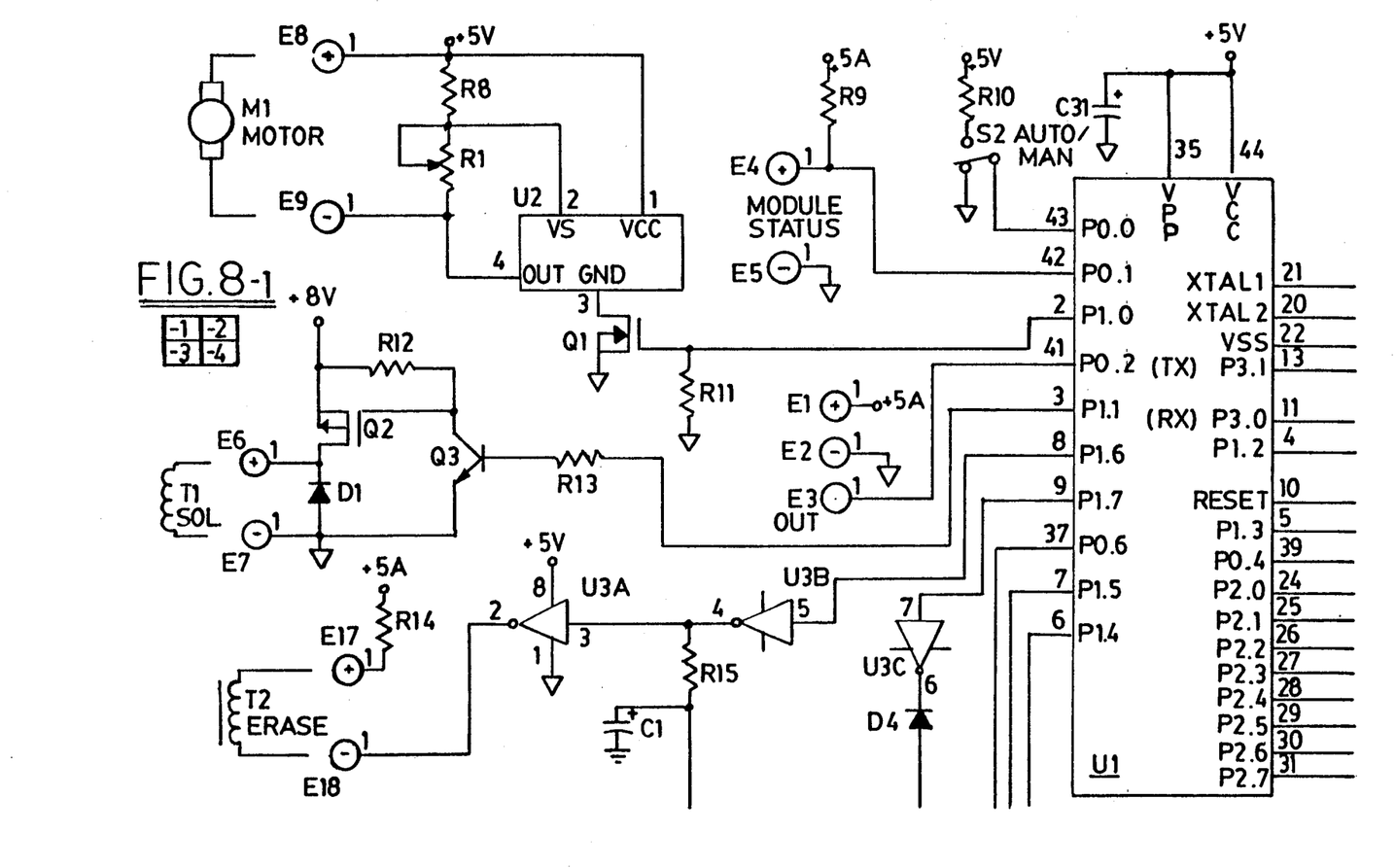

FIGS. 6 and 7 show a programming unit 13A having a cassette 22 and serial input/output connection 23 to the PTD 1. Connection 23 corresponds to a connection via switch 21, FIG. 4, to the PTD 1. The connection 24, however, is for recording from what may be termed a master cassette on the cassette of the PTD 1. What is on the cassette 22 is simply the therapist's voice recording which may be played and replayed as many times as the therapist would otherwise have to speak the same message. Such repetition by the therapist would be a waste of professional skill, time and patience.

Note that the PC of FIG. 1 could do the same thing if it were provided with a voice card, which would allow it to convert to and from disc the analog message like that on cassette 22.

A particular advantage of using a programming unit 13 instead of a PC is that it facilitates interaction between therapist and client, when they are separated geographically and a PC is not readily available to the therapist, who is vacationing perhaps. Thus, the client may want or need some change or addition in the PTD's messages. We contemplate that the therapist on such occasion will program a PTD over the phone, via phone coupler. In such case, having a programming unit while on vacation, or on any other occasion where the presence of a PC is unlikely or impractical, will allow the therapist to reprogram a PTD.

For the most part, the PTD is substantially equivalent to a number of microcassette products manufactured by Dictaphone, Panasonic, Tandy, etc., as well as to portable "walkman"-type units made for the purpose of playing music in that it contains audio electronics (speaker, amplifier circuitry, microphone), tape mechanism power supply, play button, etc. The addition of the serial port and programmable controller, however, transforms the conventional device into a powerful and versatile PTD, or the like.

Having set forth our invention as required by the statute, we claim:

What is claimed is:

1. A method of therapeutic intervention, comprising the steps of
   (1) preparing a voice record of a plurality of therapeutic intervention messages, said messages having a predetermined, fixed, semantic content for a given client, wherein said predetermined, fixed, semantic content includes material derived from interaction between said client and a therapist in the course of directing said client's attention to targeted behavior and helping said client to refocus said client's attention on certain thoughts or cognition in order to change said behavior over time;
   (2) giving said voice record to said client having a need or desire to heat at least some of said messages during times of absence from, or unavailability of, said therapist;
   (3) and at predetermined times, prompting said client to listen to certain of said messages.

2. The method of claim 1, wherein said messages are in the voice of an individual having an existing therapeutic relationship to said client, and wherein said individual provides said content, as well as any change therein, via telephone to said client for inclusion in said voice record.

3. In a process of therapeutic intervention wherein said intervention is intended to change targeted behavior of a client of a therapist; wherein said client and said therapist vocally interact with each other for targeting said behavior, and for focusing said client's attention on certain thoughts or cognitions which will aid said client to change said targeted behavior;
   wherein said client's said attention needs to be refocused periodically by such vocal interaction between said client and said therapist, whether or not said therapist is available; and
   wherein vocal interaction between said client and said therapist provides verbal material relating to said thoughts or cognitions;
   the improvement comprising the steps of
   (a) providing a message in the voice of said therapist, said message being chosen from said verbal material;
   (b) providing said client with a recording of said message, and with portable playback means for playing back said message; and
   (c) causing said message to be played back by said client, in the absence of said therapist, said client listening to said message, and reacting thereto, as if the therapist were present and client and therapist were interacting vocally, each being present to the other.

4. The invention of claim 3, wherein said client vocally reacts to said message, and said playback means includes recording means, and said client causes said recording means to record said client's vocal reaction to said message.

5. The invention of claim 3, including providing said client a plurality of messages in the voice of the therapist, and randomly spaced in time, for helping said client focus on and modify said targeted behavior.

6. A personal therapeutic device comprising, in combination, record means and playing means;
   said record means incorporating a message having a predetermined, fixed, semantic content for a given user of said therapeutic device;
   said playing means being operable by said given user for causing said playing means to play said message and to communicate its said predetermined, fixed, semantic content to said user; and
   said predetermined, fixed, semantic content including material derived from interaction between said user and a therapist in the course of directing said user's attention to targeted behavior and helping said user to refocus said user's attention on certain thoughts or cognitions in order to change said behavior over time.

7. A person therapeutic device comprising a mechanism for playing a voice record, said device also comprising audio electronics and a speaker, said mechanism being constructed and arranged for receiving a voice record having one or more therapeutic messages thereon and for playing said voice record for causing said audio electronics to make said speaker deliver a therapeutic message to a user of said device;
   said device also having a programmable control means which, when actuated by said user, controls said mechanism for causing said message to be delivered to a user of said device in accordance with a predetermined program in said programmable control means; and said one or more messages having predetermined, fixed, semantic content including material derived from interaction between a user and a therapist in the course of directing said user's attention to targeted behavior and helping said user to refocus said user's attention on certain thoughts or cognitions in order to change said behavior over time.

8. The personal therapeutic device of claim 7, including a first switch means alternatively operable for actuating said programmable control means whereby said programmable control means causes said record to be played in accordance with said predetermined program, or for preventing said programmable control means from causing said record to be played.

9. The personal therapeutic device of claim 8, including second switch means actuable for causing said message to be delivered independently of said program and of said first switch means.

10. The personal therapeutic device of claim 9 wherein said program provides for prompting said user to actuate said second switch means at predetermined time intervals when, and only when, said first switch means is actuated for causing said voice record to be played.

* * * * *

UNITED STATES PATENT AND TRADEMARK OFFICE
CERTIFICATE OF CORRECTION

PATENT NO. : 5,217,379
DATED : June 8, 1993
INVENTOR(S) : Daniel S. Kirschenbaum, Harold J. Kramer, and Mark W. Smith It is certified that error appears in the above-indentified patent and that said Letters Patent is hereby corrected as shown below:

Column 11, line 60, "heat" is hereby corrected to --hear--.

Signed and Sealed this

Fifth Day of April, 1994

Attest:

Attesting Officer

BRUCE LEHMAN

Commissioner of Patents and Trademarks